(12) United States Patent
Kim

(10) Patent No.: US 10,561,523 B2
(45) Date of Patent: Feb. 18, 2020

(54) COLLECTOR FOR HUMAN FECES

(76) Inventor: Kyoung-Hun Kim, Seoul (KR)

( * ) Notice: Subject to any disclaimer, the term of this patent is extended or adjusted under 35 U.S.C. 154(b) by 1146 days.

(21) Appl. No.: 14/371,109

(22) PCT Filed: Jan. 9, 2012

(86) PCT No.: PCT/KR2012/000192
§ 371 (c)(1),
(2), (4) Date: Jul. 8, 2014

(87) PCT Pub. No.: WO2013/105677
PCT Pub. Date: Jul. 18, 2013

(65) Prior Publication Data
US 2014/0323909 A1     Oct. 30, 2014

(51) Int. Cl.
*A61F 5/451* (2006.01)
*A61B 5/00* (2006.01)
*A61B 10/00* (2006.01)

(52) U.S. Cl.
CPC ............ *A61F 5/451* (2013.01); *A61B 5/4255* (2013.01); *A61B 10/0038* (2013.01)

(58) Field of Classification Search
CPC .. A61F 5/451; A61F 5/44; A61F 5/441; A61F 5/442; A61F 5/443; A61F 5/445; A61B 5/4255; A61B 10/0038
See application file for complete search history.

(56) References Cited

U.S. PATENT DOCUMENTS

| 4,022,212 | A  | * | 5/1977  | Lovison   | A61F 13/70 604/395 |
| 5,741,185 | A  |   | 4/1998  | Kwan et al. | |
| 6,733,482 | B1 | * | 5/2004  | Coles     | A61F 5/451 604/355 |
| 6,926,701 | B2 | * | 8/2005  | Burns, Jr. | A61F 5/451 604/277 |
| 7,819,850 | B2 | * | 10/2010 | Mullejans | A61F 5/441 604/344 |
| 8,377,020 | B1 | * | 2/2013  | Berven    | A61F 5/445 604/264 |

(Continued)

FOREIGN PATENT DOCUMENTS

| JP | 2001-087299 A | 4/2001 |
| JP | 2001-145589 A | 5/2001 |

(Continued)

*Primary Examiner* — Adam Marcetich
*Assistant Examiner* — Jessica R Arble
(74) *Attorney, Agent, or Firm* — Muncy, Geissler, Olds & Lowe, P.C.

(57) ABSTRACT

The present invention relates to a collector for human feces, consisting of: a fixing plate (100) comprising a C-shaped left plate (101) and a C-shaped right plate (101') of which the ends are connected to each other so as to have a penetrated central portion and be folded over each other; a feces collection bag (200) of which the end is fixed to one lateral side of the fixing plate (100), and which ordinarily is rolled to be inserted between the folded C-shaped left plate (101) and C-shaped right plate (101') of the fixing plate (100), and is pushed out from a penetrated hole of the fixing plate (100) when feces is injected; and an adhesion means (300). Since the feces collection bag does not come in contact with the anus when being worn, ease of defecation is facilitated due to improved comfort.

20 Claims, 8 Drawing Sheets

(56) References Cited

U.S. PATENT DOCUMENTS

| | | | |
|---|---|---|---|
| 2005/0010180 A1 | 1/2005 | Wang et al. | |
| 2006/0184144 A1* | 8/2006 | Goulden | A61B 10/0038 604/317 |
| 2009/0234312 A1* | 9/2009 | O'Toole | A61F 5/4405 604/332 |
| 2011/0040267 A1* | 2/2011 | Wada | A61F 5/455 604/318 |
| 2013/0116636 A1* | 5/2013 | Carrubba | A61F 5/445 604/318 |
| 2015/0018790 A1* | 1/2015 | Lam | A61F 5/4404 604/344 |

FOREIGN PATENT DOCUMENTS

| | | |
|---|---|---|
| KR | 10-2001-0053193 A | 6/2001 |
| KR | 10-2004-0011535 A | 2/2004 |
| KR | 10-2011-0031061 A | 3/2011 |

\* cited by examiner

[Fig. 1]
PRIOR ART
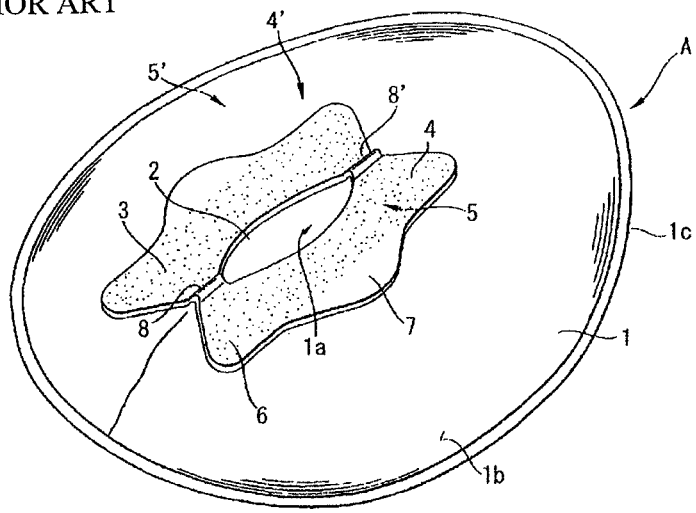
[Fig. 2]
PRIOR ART
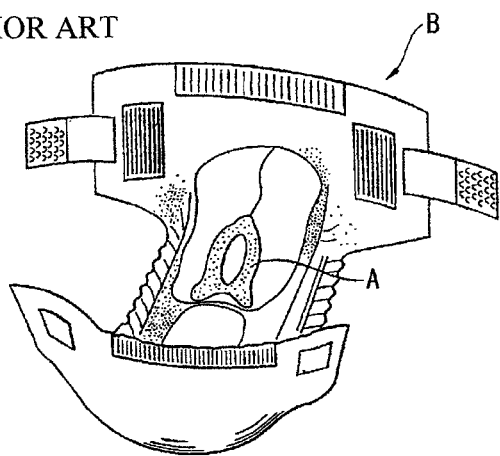

[Fig. 3]
PRIOR ART
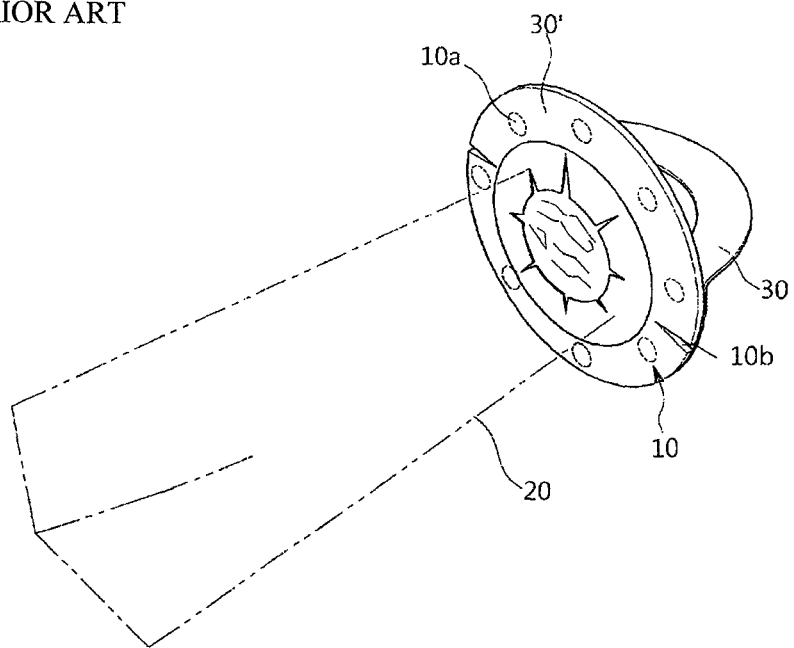
[Fig. 4]
PRIOR ART
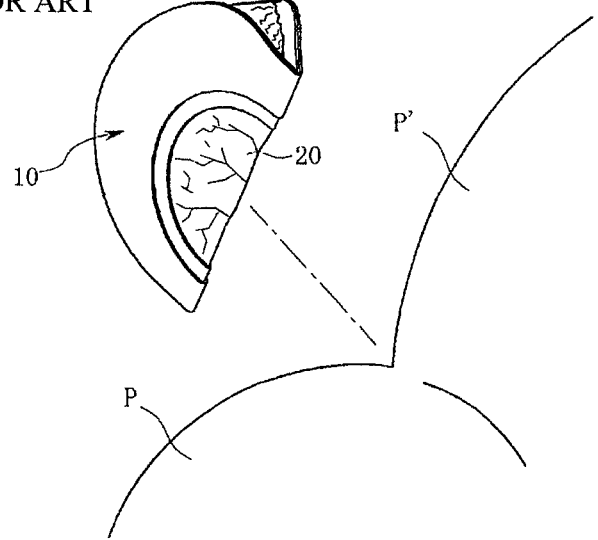

[Fig. 5]
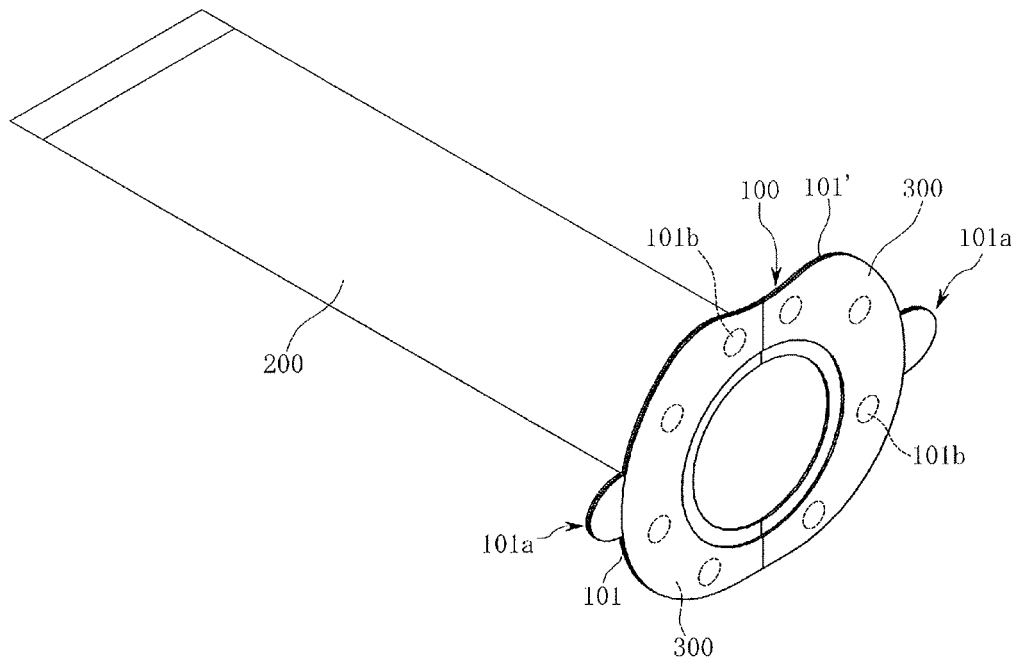
[Fig. 6]
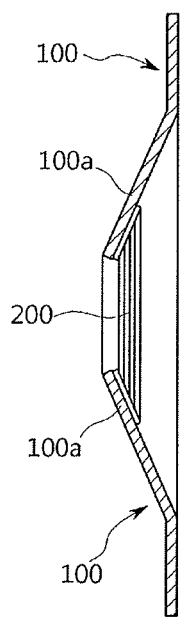

[Fig. 7]
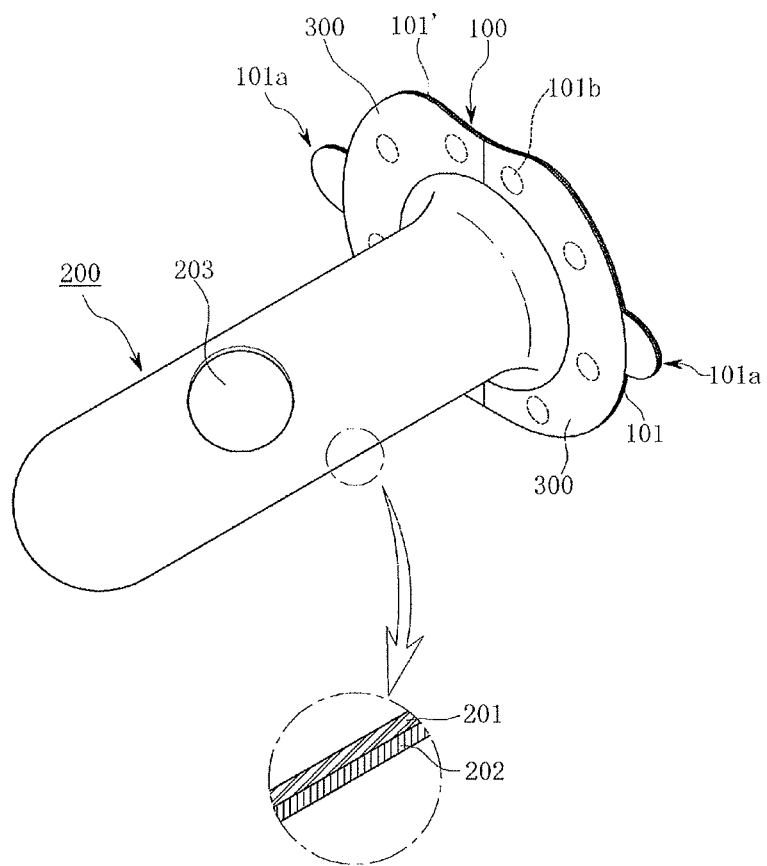
[Fig. 8]
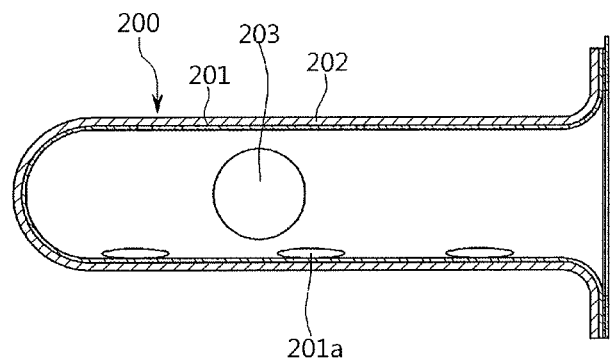

[Fig. 9]
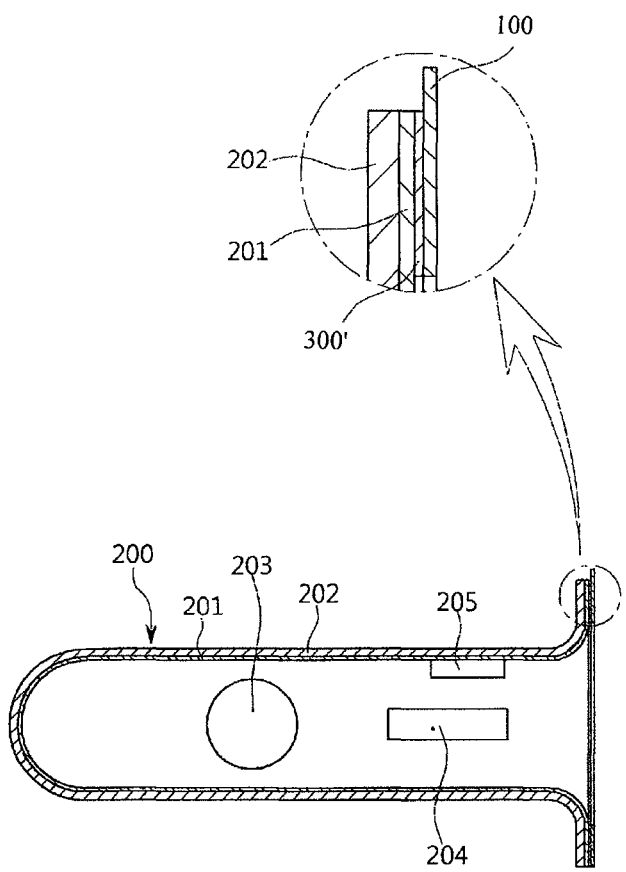
[Fig. 10a]
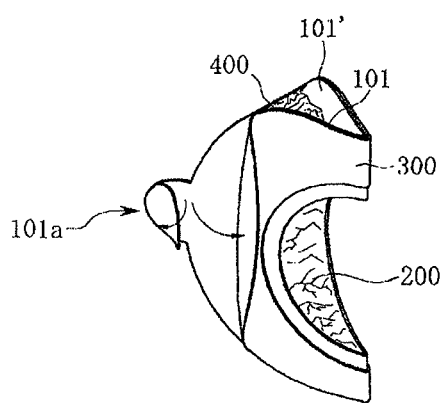

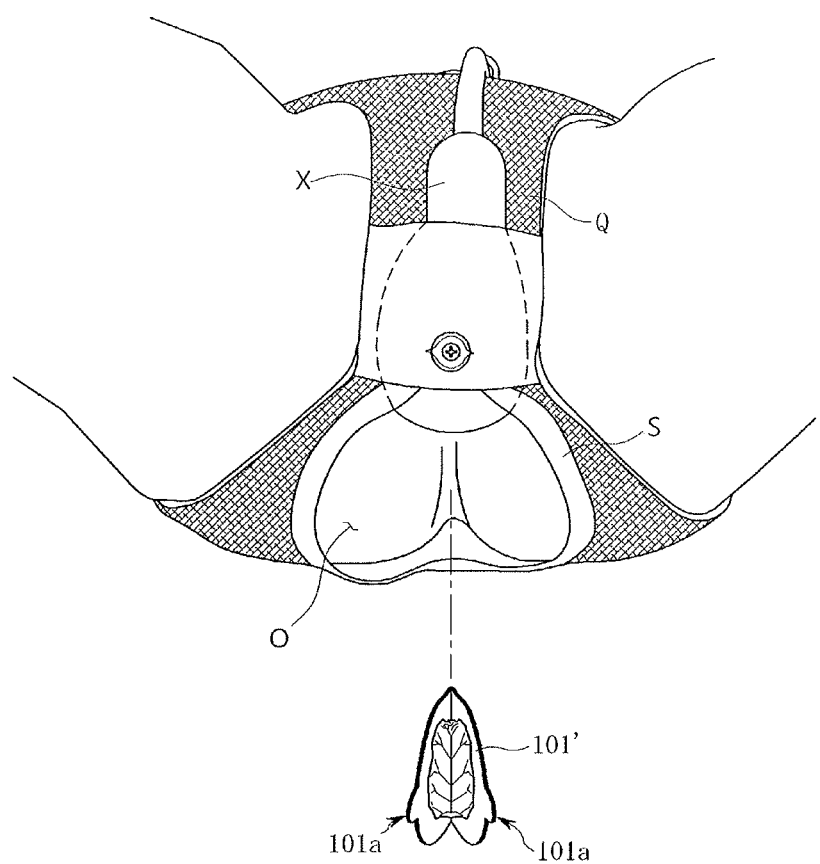
[Fig. 10b]

[Fig. 11]
[Fig. 12a]
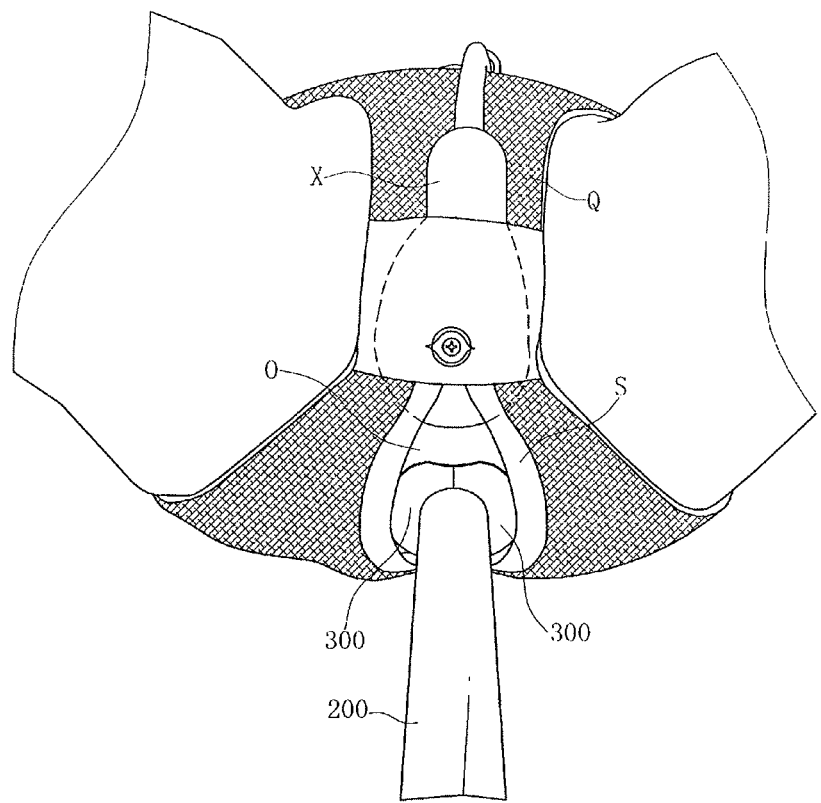
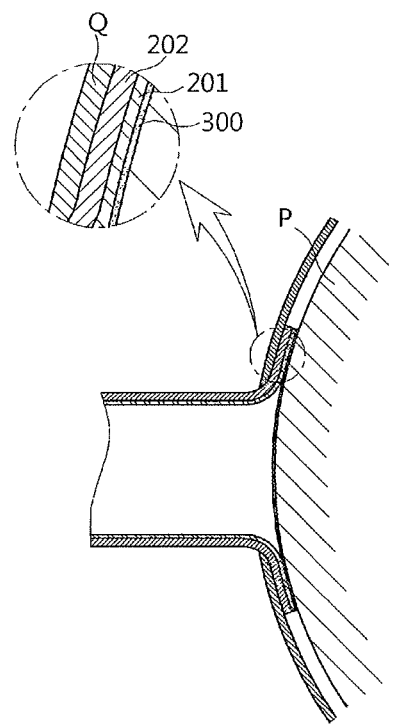

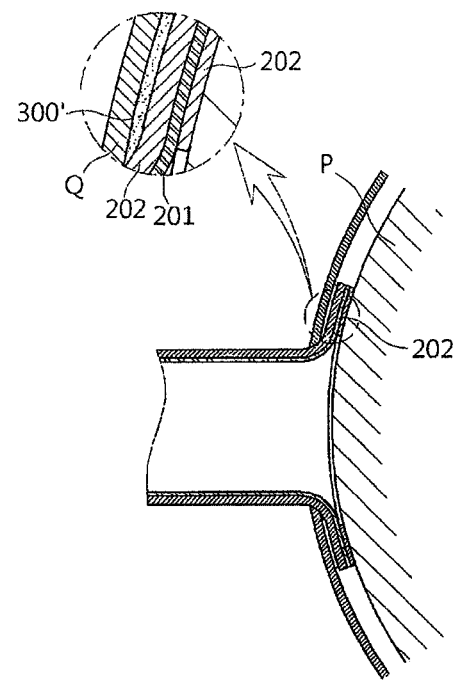
[Fig. 12b]
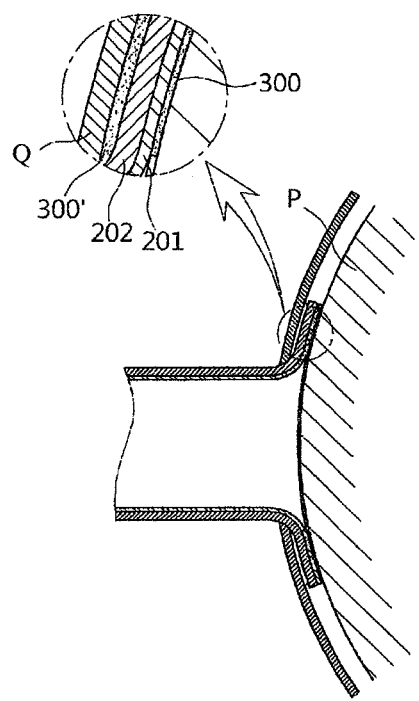
[Fig. 12c]

COLLECTOR FOR HUMAN FECES

TECHNICAL FIELD

The present invention relates, in general, to feces collectors for collecting feces of patients and, more particularly, to a collector for human feces which has a simple structure that facilitates wearing of the collector and is configured such that it can be immediately determined when a patient defecates, and a fecal occult blood test can be conducted using the small amount of blood contained in feces so that diseases the patient may have can be diagnosed and the extent of the diseases can be easily determined.

BACKGROUND ART

Generally, urine and feces disposal devices are designed to be mainly used for incontinent patients, particularly, patients who have to lie down. These urine and feces disposal devices are attached around the anus or genitals of a patient so as to directly collect and receive urine, feces and other excreta. Such disposal devices that are currently mainly used include a relatively long and narrow tube with an opening formed in an end of the tube, and a skin adhesion unit which may be an adhesive and is provided on the end of the tube.

Such disposal devices are easily twisted around the femoral region of the patient because the devices typically have a kidney shape and a relatively large size. In addition, the devices themselves may be bent or twisted. The bending or twisting of the devices naturally reduces the capacity of the devices and may induce the devices to be undesirably separated from the patient while being used, thus causing inconvenience for both the patient and caregivers.

In an effort to overcome the above problems, various techniques in which a pocket for colleting feces is formed in a disposable diaper were introduced. Particularly, a plurality of feces collectors were proposed in patent published applications, filed by "THE PROCTER & GAMBLE COMPANY."

The feces collectors introduced by "THE PROCTER & GAMBLE COMPANY" are configured to be typically used along with a diaper. A representative example of these feces collectors was proposed in Korean Patent Unexamined Publication No. 2001-53191, entitled "FECES COLLECTOR WITH IMPROVED ADHESIVE FLANGE ATTACHMENT MEANS." As shown in FIG. 1, this feces collector is a disposable feces disposal device A with a collection bag 1. Having an inner surface 1a, an outer surface 1b and a peripheral rim 1c, the collection bag 1 includes an opening 2 and a flange 3 which surrounds the opening 2. The flange 3 has a wearer skin contact surface 4 and a cloth contact surface 5. An adhesive 6 is applied to the wearer skin contact surface 4 so that the wearer skin contact surface 4 can be adhered to the perianal region of a wearer. The adhesive 6 is a substantial water-insoluble pressure-sensitive adhesive made of three-dimensional matrix polymer. The adhesive 6 contains hydrocolloid in an amount of less than 10%. The wearer skin contact surface 4 of the flange 3 includes at least one non-adhesive portion 7, and protrusions 8 and 8' which are designed to be inserted into the perineal or tailbone region of the wearer. The collection bag 1 is sealed on an outer edge thereof, and a wearer skin contact surface 4' and a cloth contact surface 5' are formed on the perimeter of the bag 1. As shown in FIG. 2, this conventional feces collector is used along with a disposable diaper B.

However, the feces collector with an improved adhesive flange attachment means of Patent Unexamined Publication No. 2001-53191 has only a function of collecting feces of the wearer and thus is disadvantageous in that a caregiver cannot easily check whether the wearer has defecated or not.

Therefore, the caregiver may not be able to rapidly dispose of the feces collector that has collected feces. In this case, the wearer may inadvertently end up wearing the feces collector for a long time with the feces collected in the feces collector. The feces in the feces collector may apply pressure to the collector so that the collector may be undesirably separated from the wearer, thus inconveniencing both the patient and a caregiver.

To solve the above problems of the conventional feces collector, a collector for human feces was proposed in Korean Patent Application No. 10-2009-0124826, filed by the applicant of the present invention.

As shown in FIG. 3, the collector for human feces according to Korean Patent Application No. 10-2009-0124826 includes a fixing plate 10 which is provided around the anus of a patient and has an opening in a central portion thereof; a feces collection bag 20 which is fixed at an end thereof to a surface of the fixing plate 10 so as to receive feces of the patient; and an adhesive means 30 which is formed on one side or both sides of the fixing plate 10. A plurality of vent holes 10a are formed in the fixing plate 10. Notches 10b are formed in a peripheral edge of the fixing plate 10 so that the fixing plate 10 can be reliably adhered to the concave perianal skin between the buttocks of the patient.

To use the collector for human feces having the above-mentioned construction according to Korean Patent Application No. 10-2009-0124826, given the structural characteristics of the human body in which the anus is linearly formed in the concave portion between the buttocks, as shown in FIG. 4, the collector is folded half such that the adhesive means 30 is oriented outwards. Thereafter, the collector is inserted into space between the buttocks P and P' of the patient, and the adhesive means 30 is adhered to the perianal skin of the patient.

However, this conventional collector for human feces is problematic in that when it is ordinarily worn around the anus of the patient, the feces collection bag 20 protrudes towards the anus through the central opening of the fixing plate 10 and makes contact with the anus of the patient, thus causing discomfort while the patient defecates.

In detail, anatomically, the anus, which forms an opening on the end of the rectum, includes the inner anal sphincter and outer anal sphincter which are covered with mucous membranes. The anal sphincters are very sensitive to touch. Therefore, when the feces collection bag 20 makes contact with the anus, the anal sphincters immediately contract, thus making it difficult for the patient to defecate.

DISCLOSURE

Technical Problem

Accordingly, the present invention has been made keeping in mind the above problems occurring in the prior art, and an object of the present invention is to provide a collector for human feces which is configured such that when the collector is worn around the anus of a patient, a feces collection bag does not make contact with the anus, thus not impeding defecation, thereby ensuring satisfactory wearability.

Another object of the present invention is to provide a collector for human feces which has a simple structure facilitating manufacture thereof and makes it possible to use a permanent girdle, rather than a disposable diaper, as a wearing assistance means, thus reducing expenses resulting from consumption of diapers and the required assistance of a caregiver.

A further object of the present invention is to provide a collector for human feces in which the feces collection bag is made of a single-layered transparent, translucent or opaque substance having characteristics of waterproof paper or has a double-layered structure, including an inner layer made of waterproof paper, and an outer layer made of water absorbent material, and in which if the feces collection bag is opaque, a transparent window is provided in the feces collection bag regardless of whether the bag has a single- or double-layered structure, whereby the caregiver can easily check conditions of defecation of the patient, and which is configured such that an ammonia sensor that detects excrement and triggers an alarm so that a caregiver can easily recognize the patient has defecated and rapidly dispose the feces, thus preventing the feces collector from being undesirably separated from the patient because of a delay in feces disposal, thereby preventing the patient, the patient's clothes, bedding, etc. from being contaminated with feces.

Yet another object of the present invention is to provide a collector for human feces in which an occult blood test paper is attached to a portion of an inner surface of the collector, whereby a fecal occult blood test can be conducted using a small amount of blood contained in the feces so that diseases the patient may have can be diagnosed and the extent of such diseases can be easily checked, and which is provided with a cancer indication sensor for detecting cancer-related substances, thus making it possible to diagnose cancer such as colorectal cancer.

Technical Solution

In order to accomplish the above objects, the present invention provides a collector for human feces including: a fixing plate (100) including a C-shaped left plate (101) and a C-shaped right plate (101') connected at ends thereof to each other so as to be foldable onto each other, with a opening defined in a central portion of the fixing plate 100 by the C-shaped left and right plates (101) and (101'); a feces collection bag (200) fixed at an end thereof to a first surface of the fixing plate (100) and ordinarily rolled and disposed between the folded C-shaped left and right plates (101) and (101') of the fixing plate (100), the feces collection bag (200) being configured to be pushed out from the opening of the fixing plate (100) when feces is injected into the feces collection bag (200); and an adhesive means (300) formed on a second surface of the fixing plate (100).

Advantageous Effects

A collector for human feces according to the present invention is configured such that when the collector is worn around the anus of a patient, a feces collection bag does not make contact with the anus, thus not impeding defecation, thereby ensuring satisfactory wearability. The collector for human feces has a simple structure facilitating manufacture thereof and makes it possible to use a permanent girdle, rather than a disposable diaper, as a wearing assistance means, thus reducing expenses resulting from consumption of diapers and the required assistance of a caregiver. A transparent window is provided on the feces collection bag, whereby a caregiver can easily ascertain whether or not the patient has defecated. Furthermore, an ammonia sensor detects excrement and triggers an alarm so that a caregiver can easily recognize the patient has defecated and rapidly dispose of the feces, thus preventing the feces collector from being undesirably separated from the patient because of a delay of feces disposal, thereby preventing the patient, the patient's clothes, bedding, etc. from being contaminated with feces. In addition, an occult blood test paper is attached to a portion of an inner surface of the collector. Thus, a fecal occult blood test can be conducted using a small amount of blood contained in the feces so that diseases the patient may have can be diagnosed and the extent of such diseases can be easily checked. Further, the collector is provided with a cancer indication sensor for detecting cancer-related substances, thus making it possible to diagnose cancer such as colorectal cancer.

DESCRIPTION OF DRAWINGS

FIG. 1 is a perspective view showing a conventional feces disposal device;

FIG. 2 is a perspective view showing the conventional feces disposal device combined with a disposal diaper;

FIG. 3 is a perspective view showing a conventional human feces collector proposed by the applicant of the present invention;

FIG. 4 is a view illustrating a method of wearing the conventional human feces collector proposed by the applicant of the present invention;

FIG. 5 is a perspective view illustrating a collector for human feces according to the present invention;

FIG. 6 is a sectional view showing another embodiment of the collector for human feces according to the present invention;

FIG. 7 is a perspective view of an embodiment of a collector for human feces according to the present invention;

FIG. 8 is a view showing a superabsorbent polymer member provided on a surface of an inner layer according to an embodiment of the present invention;

FIG. 9 is a sectional view illustrating an embodiment of a collector for human feces according to the present invention;

FIGS. 10*a* and 10*b* are views illustrating a method of wearing a collector for human feces according to the present invention;

FIG. 11 is a view showing the feces human collector worn by a patient according to the present invention; and FIGS. 12*a* through 12*c* are sectional views showing use of embodiments of the feces human collector according to the present invention.

BEST MODE

Hereinafter, preferred embodiments of a collector for human feces according to the present invention will be described in detail with reference to the attached drawings.

The collector for human feces according to an embodiment of the present invention includes: a fixing plate 100 which includes a C-shaped left plate 101 and a C-shaped right plate 101' which are connected at ends thereof to each other so as to be foldable onto each other, with an opening defined in a central portion of the fixing plate 100 by the C-shaped left and right plates 101 and 101'; a feces collection bag 200 which is fixed at an end thereof to a first surface of the fixing plate 100 and is ordinarily in a compacted state, e.g., rolled, and disposed between the folded C-shaped left and right plates 101 and 101' of the fixing plate 100, and is configured to be pushed out from the opening of the fixing plate 100 when feces is injected into the feces collection bag 200; and an adhesive means 300 which is formed on a second surface of the fixing plate 100.

The collector for human feces according to an embodiment of the present invention further includes an tearable film 400 which is provided between an outer edge of the C-shaped left plate 101 and an outer edge of the C-shaped right plate 101' while the C-shaped left plate 101 and the C-shaped right plate 101' of the fixing plate 100 are in a folded state with a predetermined distance therebetween. The tearable film 400 is configured such that, when feces is injected into the feces collection bag 200, the tearable film 400 is punctured by the feces. The feces collection bag 200, which is folded and rolled, is disposed in space defined among the C-shaped left plate 101, the C-shaped right plate 101' and the tearable film 400.

The fixing plate 100, having an opening in a central portion thereof, is formed in a shape selected from among a circular plate shape, an elliptical plate shape, a polygonal plate shape and a shape of a closed curve plate such as a heart-shaped plate. Preferably, handles 101a are respectively provided on left and right edges of the fixing plate 100. Furthermore, it is preferable that the fixing plate 100 be made of elastic or inelastic felt, a medical adhesive sheet or fiber muscle tape which is breathable, or a material having a plurality of fine vent holes. If the material for the fixing plate 100 is not breathable, a plurality of vent holes 101b may be formed in the fixing plate 100.

Preferably, the junction between the C-shaped left plate 101 and the C-shaped right plate 101' of the fixing plate 100 includes a folding part so that the fixing plate 100 can be adhered to a concave perianal skin between the buttocks of the patient.

As shown in FIG. 6, preferably, the fixing plate 100 has a bent portion 100a which is formed by bending a central portion of the fixing plate 100 in a direction so that the feces collection bag 200 does not come into contact with the skin of the patient when the fixing plate 100 is adhered to the concave perianal skin between the buttocks of the patient. The feces collection bag 200 is attached to an end of an inner surface of the bent portion 100a. In this case, the feces collection bag 200 may have a bellows structure.

A plurality of lattice folding lines are formed in the entirety of the surface of the collection bag 200 so that when the collector is not being worn, the feces collection bag 200 is maintained in the compacted state, e.g., a folded and rolled state, between the C-shaped left plate 101 and the C-shaped right plate 101', and when the collector is being worn, the feces collection bag 200 does not come into contact with the skin of the patient.

The feces collection bag 200 is preferably made of a biodegradable vinyl which biodegrades after a predetermined period of time has passed. The feces collection bag 200 may be configured to have a single-layered structure using transparent, translucent or opaque material.

As shown in FIG. 7, the feces collection bag 200 includes an inner layer 201 made of waterproof paper, and an outer layer 202 made of water absorbent felt. Preferably, a transparent window 203 which allows a caregiver to visually check whether the patient has defecated is formed in the outer layer 202.

As shown in the FIG. 8, to absorb water from feces while the patient defecates, the feces collection bag 200 may include at least one super absorbent polymer (SAP) member 201a which is adhered to the inner layer 201 in such a way that the SAP member 201a is disposed on a lower portion of the feces collection bag 200 when the collector is worn by the patient. Alternatively, a super absorbent polymer (SAP) film may be applied to the surface of the inner layer 201 of the feces collection bag 200.

Furthermore, an occult blood test paper 204 may be adhered to a portion of the inner surface of the inner layer 201 of the feces collection bag 200 or the fixing plate 100, thus enabling the testing of occult blood contained in the feces and allowing convenient checking of diseases the patient may have. A cancer indication sensor which detects cancer-related substances and makes it possible to diagnose cancer such as colorectal cancer may be installed on the inner layer 201. In addition, connected to an alarm device, a defecation sensor 205 which senses feces may be installed on the inner layer 201, so that the presence of feces can trigger the alarm device.

Various sensors can be used as the defecation sensor 205 to sense whether the patient has defecated and to trigger the alarm. For example, an ammonia sensor which senses ammonia in feces, a pressure sensor which senses variation in pressure caused by feces in the feces collection bag 200, a humidity sensor which senses variation in humidity caused by feces in the feces collection bag 200, a light sensor which senses whether light is blocked by feces, an electrode sensor which senses whether electrodes are connected to each other by feces, etc. can be used as the defecation sensor 205.

The adhesive means 300 may be directly adhered to the perianal skin of the patient or, alternatively, to a girdle which is open on a portion thereof corresponding to the anus of the patient. Another adhesive means 300' may be formed in an edge of the fixing plate 100 that is adjacent to the feces collection bag 200. In this case, the adhesive means 300 is directly adhered to the perianal skin of the patient, while the adhesive means 300' is adhered to a girdle which is open on a portion thereof corresponding to the anus of the patient.

If only the adhesive means 300' is present without the adhesive means 300, a portion of the fixing plate 100 which comes into contact with the skin of the patient is preferably coated with the outer layer 202 so as to protect a portion of the skin of the patient that makes contact with the fixing plate 100.

Hereinafter, the operation and use of the collector for human feces according to the present invention having the above-mentioned construction will be described in detail.

As shown in FIG. 10a, when the collector for human feces according to the present invention is produced, the fixing plate 100 is in the folded state in such a way that the C-shaped left plate 101 and the C-shaped right plate 101' are spaced apart from each other by a predetermined distance. Preferably, the predetermined distance is set in consideration of the anatomic structure of the human body, that is, the distance between the left and right buttocks between which the anus is located.

In FIG. 10a, although adhesive tape is illustrated as being used as the adhesive means 300, this is only for the sake of explanation, and other various adhesive means can be employed.

To wear the collector for human feces according to the present invention, as shown in FIG. 10a, a user grasps the handle 101a of the collector and then removes a release paper of the adhesive tape which is the adhesive means 300. Subsequently, as shown in FIG. 10b, the collector is pushed and inserted into the space between the buttocks of the patient, and the adhesive means 300 is adhered to the perianal skin.

FIG. 10b illustrates a urine collection device X, along with the collector for human feces according to the present invention, worn using a girdle Q. In FIG. 10b, the reference character O denotes an opening, and S denotes an elastic material part of the girdle Q.

In this way, as shown in FIG. 11, the collector for human feces according to the present invention can be worn. In this case, as shown in FIGS. 10b, 11 and 12A, the adhesive means 300 is directly adhered to the perianal skin p of the patient. In addition, the girdle O does not adhere to the collector according to the present invention, and the elastic material part S of the girdle Q defines the opening O while covering the fixing plate 100 or not covering it.

In this state, when the patient defecates, feces is injected into the feces collection bag 200. At this time, the tearable film 400 is punctured by the feces injected into the feces collection bag 200, and the feces collection bag 200 is pushed by the feces in the direction opposite to the anus. The feces that has passed through the punctured portion of the tearable film 400 is collected in the feces collection bag 200.

If the feces collection bag 200 is formed of a transparent material, conditions of the defecation can be directly checked. If the feces collection bag 200 is formed of an opaque material or has a double-layered structure, a caregiver can easily visually check conditions of the defecation through the transparent window 203. Furthermore, the defecation sensor 205, such as the ammonia sensor, the pressure sensor, the humidity sensor, the light sensor or the electrode sensor, senses feces and transmits a sensing signal to an alarm device, for example, of the urine collection device X, which is an electronic product. Then, the alarm device generates an alarm, whereby a caregiver can easily recognize that the patient has defecated.

In addition, the occult blood of feces can be tested by checking a variation in color of the occult blood test paper 204 adhered to the inner surface of the inner layer 201, whereby diseases the patient may have can be checked. The cancer indication sensor installed in the inner surface of the inner layer 201 can sense cancer-related substances, thus making it possible to diagnose cancer such as colorectal cancer.

FIG. 12b is a sectional view showing use of another embodiment of the collector for human feces according to the present invention. In this embodiment, without the adhesive means 300, the adhesive means 300' is adhered to the girdle Q, so that the patient can use the collector for human feces by means of wearing the girdle Q.

In the same manner mentioned above, when the patient defecates, a caregiver can easily visually check the defecation through the transparent window 203. Also, the caregiver can easily recognize that the patient has defecated via the defecation sensor 205 sensing the feces, transmitting a sensing signal to the alarm device, and instructing the alarm device to generate an alarm.

Furthermore, the occult blood of feces is tested by checking a variation in color of the occult blood test paper 204 adhered to the inner surface of the inner layer 201, whereby diseases the patient may have can be checked. The cancer indication sensor installed on the inner surface of the inner layer 201 senses cancer-related substances, thus making it possible to diagnose cancer such as colorectal cancer.

FIG. 12c is sectional view showing use of a further embodiment of the collector for human feces according to the invention.

In this embodiment, not only is the adhesive means 300 directly adhered to the perianal skin P of the patient, but the adhesive means 300' is also adhered to the girdle Q. In the same manner mentioned above, when the patient defecates, a caregiver can easily visually check the defecation through the transparent window 203. Also, the caregiver can easily recognize that the patient has defecated via the defecation sensor 205 sensing the feces, transmitting a sensing signal to the alarm device, and instructing the alarm device to generate an alarm.

Furthermore, the occult blood of feces is tested by checking a variation in color of the occult blood test paper 204 adhered to the inner surface of the inner layer 201, whereby diseases the patient may have can be checked. The cancer indication sensor installed on the inner surface of the inner layer 201 senses cancer-related substances, thus making it possible to diagnose cancer such as colorectal cancer.

Although the preferred embodiment of the present invention has been disclosed, those skilled in the art will appreciate that various modifications, additions and substitutions are possible, without departing from the scope and spirit of the invention.

The invention claimed is:

1. A collector for human feces comprising:
a fixing plate (100) including a C-shaped left plate (101) and a C-shaped right plate (101') connected at ends thereof to each other so as to be foldable onto each other, with an opening defined in a central portion of the fixing plate (100) by the C-shaped left and right plates (101) and (101');
an adhesive means (300 or 300') formed on the fixing plate (100) to affix the fixing plate (100) to a patient or a garment worn by the patient or both, so that the opening overlies an anus of the patient; and
a feces collection bag (200) fixed at an end thereof to the fixing plate (100), wherein when the feces collection bag (200) is in a compacted state between the folded C-shaped left and right plates (101 and (101') of the fixing plate (100), the feces collection bag (200) does not make contact with the anus of the patient while the collector is worn by the patient, and wherein the feces collection bag (200) is configured to be pushed out from the opening of the fixing plate (100) when feces is injected into the feces collection bag (200), wherein the fixing plate (100) has a bent portion (100a) formed by bending the central portion of the fixing plate (100) in a direction away from the patient so that the feces collection bag (200) is spaced further from the anus of the patient; and
a tearable film (400) provided between an outer edge of the C-shaped left plate (101) and an outer edge of the C-shaped right plate (101') while the C-shaped left plate (101) and the C-shaped right plate (101') of the fixing plate (100) are in a folded state with a predetermined distance therebetween, the tearable film (400) being configured such that, when feces is injected into the feces collection bag (200), the tearable film (400) is torn by the feces.

2. The collector for human feces as set forth in claim 1, wherein the fixing plate (100) includes handles (101a) respectively provided on left and right edges of the fixing plate (100) and is made of any one of an elastic or inelastic felt, a medical adhesive sheet and fiber muscle tape that are breathable, or the fixing plate (100) comprises any one of a circular plate, an elliptical plate, a polygonal plate and a closed curve plate, each of which has a plurality of vent holes with an opening formed in a central portion thereof.

3. The collector for human feces as set forth in claim 1, wherein the feces collection bag (200) is attached to an end of an inner surface of the bent portion (100a).

4. The collector for human feces as set forth in claim 1, wherein a junction between the C-shaped left plate (101) and the C-shaped right plate (101') of the fixing plate (100) comprises a folding part so that the fixing plate (100) can be adhered to the perianal skin, which is concave between a buttocks of the patient.

5. The collector for human feces as set forth in claim 1, wherein a plurality of lattice folding lines are formed in an entirety of a surface of the feces collection bag (200) so that when the collector is not being worn, the feces collection bag (200) is maintained in the compacted state between the C-shaped left plate (101) and the C-shaped right plate (101').

6. The collector for human feces as set forth in claim 1, wherein the feces collection bag (200) has a bellows structure to form the compacted state.

7. The collector for human feces as set forth in claim 1, wherein the feces collection bag (200) is made of biodegradable vinyl that biodegrades after a predetermined period of time has passed.

8. The collector for human feces as set forth in claim 1, wherein the feces collection bag (200) has a single-layered structure and is made of transparent, translucent or opaque material.

9. The collector for human feces as set forth in claim 1, wherein the feces collection bag (200) has a double-layered structure including a waterproof inner layer (201) and a water absorbent outer layer (202).

10. The collector for human feces as set forth in claim 8, wherein when the feces collection bag (200) is made of the opaque material not allowing observation of an interior of the feces collection bag (200), a transparent window (203) is formed in the feces collection bag (200), the transparent window (203) allowing visual checking of whether feces is present and conditions of defecation.

11. The collector for human feces as set forth in claim 1, wherein the feces collection bag (200) comprises, to absorb water contained in the feces, at least one super absorbent polymer (SAP) member (201a) provided on an inner layer (201) of the feces collection bag (200), the SAP member (201a) being disposed on a lower portion of the feces collection bag (200) when the collector is worn, or a super absorbent polymer (SAP) film applied to a surface of the inner layer (201).

12. The collector for human feces as set forth in claim 1, wherein an occult blood test paper (204) is provided on a portion of an inner surface of an inner layer (201) of the feces collection bag (200), the occult blood test paper (204) enabling testing of occult blood contained in the feces.

13. The collector for human feces as set forth in claim 1, wherein an occult blood test paper (204) is provided on a portion of an inner surface of the fixing plate (100), the occult blood test paper (204) enabling testing of occult blood contained in the feces.

14. The collector for human feces as set forth in claim 1, wherein an indication sensor is provided on a portion of an inner surface of an inner layer (201) of the feces collection bag (200), the indication sensor detecting cancer-related substances.

15. The collector for human feces as set forth in claim 1, wherein an indication sensor is provided on a portion of an inner surface of the fixing plate (100), the indication sensor detecting cancer-related substances.

16. The collector for human feces as set forth in claim 1, wherein a defecation sensor (205) is provided on a portion of an inner surface of an inner layer of the feces collection bag (200), the defecation sensor (205) being connected to an alarm device to trigger the alarm device to generate an alarm when a patient defecates.

17. The collector for human feces as set forth in claim 1, wherein a defecation sensor (205) is provided on a portion of an inner surface of the fixing plate (100), the defecation sensor (205) being connected to an alarm device to trigger the alarm device to generate an alarm when a patient defecates.

18. The collector for human feces as set forth in claim 16, wherein the defecation sensor (205) comprises any one of an ammonia sensor, a pressure sensor, a humidity sensor, an optical sensor and an electrode sensor.

19. The collector for human feces as set forth in claim 1, wherein the adhesive means (300 or 300') is directly adhered to a perianal skin of the patient or a girdle having an opening at a position corresponding to the anus of the patient.

20. The collector for human feces as set forth in claim 1, wherein the adhesive means (300 or 300') is a first adhesive means (300), and wherein a second adhesive means (300') is formed on an edge of the fixing plate (100) at a position adjacent to the feces collection bag (200) so that the first adhesive means (300) is directly adhered to a perianal skin of the patient, while the second adhesive means (300') is adhered to a girdle having an opening at a position corresponding to the anus of the patient.

* * * * *